(12) United States Patent
Kincaid

(10) Patent No.: US 7,825,929 B2
(45) Date of Patent: *Nov. 2, 2010

(54) SYSTEMS, TOOLS AND METHODS FOR FOCUS AND CONTEXT VIEWING OF LARGE COLLECTIONS OF GRAPHS

(75) Inventor: Robert Kincaid, Half Moon Bay, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/124,500

(22) Filed: May 6, 2005

(65) Prior Publication Data
US 2005/0206644 A1 Sep. 22, 2005

Related U.S. Application Data

(63) Continuation-in-part of application No. 10/964,524, filed on Oct. 12, 2004, which is a continuation-in-part of application No. 10/817,244, filed on Apr. 3, 2004.

(60) Provisional application No. 60/460,479, filed on Apr. 4, 2003.

(51) Int. Cl.
*G06T 11/20* (2006.01)
*G09G 5/22* (2006.01)

(52) U.S. Cl. .................. 345/440; 345/440.1; 345/440.2

(58) Field of Classification Search .................. 345/440, 345/660, 440.1, 440.2
See application file for complete search history.

(56) References Cited

U.S. PATENT DOCUMENTS 3,599,033 A * 8/1971 Stettiner et al. ............. 315/384

(Continued)

FOREIGN PATENT DOCUMENTS

WO 0127809 4/2001

OTHER PUBLICATIONS

Autio, et al. CGH-Plotor: MATLAB toolbox forcGH-data analysisd', Bioinformatices, vol. 19 No. 13 2003, pp. 1714-1715.*

(Continued)

*Primary Examiner*—Ulka Chauhan
*Assistant Examiner*—Jeffrey J Chow

(57) ABSTRACT

Systems, tools, methods and computer readable media for visualizing a collection of graphs to provide context and focus. A compressed visualization is formed by compressing all of the graphs in a direction along a compression axis of the visualization. At least one of the compressed graphs may be zoomed to make a visualization of the at least one graph having a greater scale along the second axis than a scale of the compressed graphs. The zoomed graph or graphs may be displayed along with the compressed graphs, wherein the zoomed graph or graphs are displayed in a same order relative to the compressed graphs and each other as occupied prior to the zooming. A user interface for use in visualizing a collection of graphs in an overall view while at the same time providing the ability to view detail with regard to at least one of the graphs includes a display configured to visualize the collection of graphs in compressed form, and a feature for selecting a graph from the visualization of the compressed collection, wherein upon selecting a graph, the interface zooms at least the selected graph to make a visualization of at least the selected graph having a greater scale along an axis of compression of the compressed visualization than a scale of the compressed graphs along the axis of compression. The selected graph and any other zoomed graphs may be displayed in the same order that they occupied in the compressed visualization, relative to the graphs remaining compressed and each other.

34 Claims, 9 Drawing Sheets
(5 of 9 Drawing Sheet(s) Filed in Color)

U.S. PATENT DOCUMENTS

| Patent No. | | | Date | Inventor | Class |
|---|---|---|---|---|---|
| 5,226,118 | A | * | 7/1993 | Baker et al. | 715/833 |
| 5,228,119 | A | * | 7/1993 | Mihalisin et al. | 345/418 |
| 5,530,373 | A | * | 6/1996 | Gibson et al. | 324/758 |
| 5,632,009 | A | * | 5/1997 | Rao et al. | 715/509 |
| 5,684,507 | A | * | 11/1997 | Rasnake et al. | 345/440.1 |
| 5,684,508 | A | * | 11/1997 | Brilman | 345/440.1 |
| 5,830,150 | A | * | 11/1998 | Palmer et al. | 600/523 |
| 5,895,474 | A | * | 4/1999 | Maarek et al. | 715/514 |
| 5,929,842 | A | * | 7/1999 | Vertregt et al. | 345/690 |
| 5,966,139 | A | * | 10/1999 | Anupam et al. | 345/440 |
| 6,064,401 | A | * | 5/2000 | Holzman et al. | 345/440 |
| 6,171,797 | B1 | | 1/2001 | Perbost | |
| 6,180,351 | B1 | | 1/2001 | Cattell | |
| 6,188,783 | B1 | | 2/2001 | Balaban et al. | |
| 6,219,052 | B1 | * | 4/2001 | Gould | 345/661 |
| 6,221,583 | B1 | | 4/2001 | Kayyem et al. | |
| 6,222,664 | B1 | | 4/2001 | Dorsel | |
| 6,232,072 | B1 | | 5/2001 | Fisher | |
| 6,242,266 | B1 | | 6/2001 | Schleifer et al. | |
| 6,251,685 | B1 | | 6/2001 | Dorsel et al. | |
| 6,320,196 | B1 | | 11/2001 | Dorsel et al. | |
| 6,323,043 | B1 | | 11/2001 | Caren et al. | |
| 6,355,921 | B1 | | 3/2002 | Staton et al. | |
| 6,356,285 | B1 | * | 3/2002 | Burkwald et al. | 715/853 |
| 6,371,370 | B2 | | 4/2002 | Sadler et al. | |
| 6,406,849 | B1 | | 6/2002 | Dorsel et al. | |
| 6,424,973 | B1 | | 7/2002 | Kendall et al. | |
| 6,486,457 | B1 | | 11/2002 | Dorsel et al. | |
| 6,518,556 | B2 | | 2/2003 | Staton et al. | |
| 6,628,312 | B1 | * | 9/2003 | Rao et al. | 715/853 |
| 6,711,577 | B1 | * | 3/2004 | Wong et al. | 707/101 |
| 6,776,342 | B1 | * | 8/2004 | Thuries et al. | 235/462.15 |
| 7,035,739 | B2 | | 4/2006 | Schadt | |
| 7,038,680 | B2 | * | 5/2006 | Pitkow | 345/440 |
| 7,118,853 | B2 | | 10/2006 | Botstein | |
| 7,243,112 | B2 | | 7/2007 | Qu | |
| 7,472,137 | B2 | | 12/2008 | Edelstein et al. | |
| 2002/0004489 | A1 | | 1/2002 | Shi et al. | |
| 2002/0174096 | A1 | | 11/2002 | O'Reilly et al. | |
| 2003/0009295 | A1 | | 1/2003 | Markowitz et al. | |
| 2003/0065535 | A1 | * | 4/2003 | Karlov et al. | 705/2 |
| 2003/0211484 | A1 | | 11/2003 | Ben-Dor et al. | |
| 2004/0080536 | A1 | | 4/2004 | Yakhini et al. | |
| 2004/0095349 | A1 | * | 5/2004 | Bito et al. | 345/440 |
| 2004/0163039 | A1 | * | 8/2004 | Gorman | 715/505 |
| 2005/0027729 | A1 | * | 2/2005 | Kuchinsky et al. | 707/100 |
| 2005/0034107 | A1 | | 2/2005 | Baclawski | |
| 2005/0048569 | A1 | * | 3/2005 | Van Der Spek et al. | 435/7.1 |
| 2005/0068322 | A1 | * | 3/2005 | Falcioni | 345/467 |
| 2005/0228735 | A1 | * | 10/2005 | Duquette | 705/37 |
| 2006/0020398 | A1 | * | 1/2006 | Vernon et al. | 702/20 |

OTHER PUBLICATIONS

M. S. T. Carpendale, Catherine Montagnese. Papers: Information visualization'. "A framework for unifying presentation soace". Nov. 2001 . Proceedinns of the 14th annual ACM symposium on User inteface software and technology.*

Moore, et al.,"A t-statistic for Objective Interpretation of Comparative Genomic Hybridization (CGH),"Profiles, Cytometry, vol. 28, pp. 183-190, 1997.*

Pollack et al., "Microarray analysis reveals a major direct role of DNA copy number alteration in the transcriptional program of human breast tumors" PNAS, Oct. 1, 2002, vol. 99, No. 20, 12993-12968.*

Figure from www.firstcap.com, http://www.firstcap.com/fco2001. gif.*

Figure from www.kirin.co.jp, http://www.kirin.co.jp/english/annual2001/images/26info/26_graph.gif.*

Miller, Bill, "MatLab Taining Course Notes: Session3", http://dnl.ucsf.edu/matlab/session3.html, Jun. 16, 2001.*

Hedenfalk et al.,"Molecular classification of familial non-BRCA1/BRCA2 breast cancer", PNAS. Mar. 4, 2003, vol. 100, No. 5, 2532-2537.

Ben-Dor et al., "Class Discovery in Gene Expression Data", Fifth Annual International Conference on Computational Molecular Biology, 2001, pp. 31-38.

Wang, et al. "Statistical Methods for Detecting Genomic Alterations Through Array-Based Comparative Genomic Hybridization (CGH)," Frontiers in Bioscience, vol. 9, pp. 540-549, 2004.

Carothers, "A likelihood-based approach to the estimation of relative DNA copy number by comparative genomic hybridization," Biometrics, vol. 53, pp. 848-856, 1997.

Crawley, et al., "Identification of Frequent Cytogenetic Aberrations in Hepatocellular Carcinoma Using Gen-Expression Microarry Data," Genome Biol, vol. 3, pp. Research0075, 2002.

Ben-Dor, et al., "Analysis of Array Based Comparative Genomic Hybridization Data—Theory and Validation," pp. 1-10. Not dated.

Jong, et al. "Breakpoint Identification and Smoothing of Array Comparative Genomic Hybridization data," pp. 1-2, 2004.

Rohatgi, in Statistical Inference. Mineola, New York: Dover Publications, Inc., 2003, 4 pgs.

Silicon Genetics, "Predictive Tools (Machine Learning Algorithms)", http://www.silicongenetics.com/cgi/SiG.cgi/Products/GeneSpring/predict.smf?, p. 1, downloaded Jul. 15, 2002.

Silicon Genetics, "Hierarchical Clustering: Tree Building", http://www.silicongenetics.com/cgi/SiG.cgi/Products/GeneSpring/predict.smf?, p. 1, downloaded Jul. 15, 2002.

Silicon Genetics, "k-means Clustering", http://www.silicongenetics.com/cgi/SiG.cgi/Products/GeneSpring/Kmeans.smf?, p. 1, downloaded Jul. 15, 2002.

Silicon Genetics, "Self-organizing Maps", http://www.silicongenetics.com/cgi/SiG.cgi/Products/GeneSpring/SOM.smf?, p. 1, downloaded Jul. 15, 2002.

Silicon Genetics, "Principal Components Analysis", http://www.silicongenetics.com/cgi/SiG.cgi/Products/GeneSpring/PCA.smf?, pp. 1-2, downloaded Jul. 15, 2002.

Silicon Genetics, "Regulatory Sequence Search", http://www.silicongenetics.com/cgi/SiG.cgi/Products/GeneSpring/RegSeq.smf?, p. 1, downloaded Jul. 15, 2002.

Silicon Genetics, "Similarity Metrics", http://www.silicongenetics.com/cgi/SiG.cgi/Products/GeneSpring/sim_metrics.smf?, p. 1, downloaded Jul. 15, 2002.

"GeneSpring", www.silicongenetics.com, pp. 1-2, downloaded Nov. 22, 2002.

Ben-Dor et al., "Tissue Classification with Gene Expression Profiles", J. Computational Biology, 2000, pp. 1-32.

Fujii et al., "A Preliminary Transcriptome Map of Non-Small Cell Lung Cancer", Cancer Reserch 62, 3340-3346, Jun. 15, 2002.

Silicon Genetics, "Filtering Tools", http://www.silicongenetics.com/cgi/cgi/SiG.cgi/Products/GeneSpring/filter.smf?, p. 1, downloaded Jul. 15, 2002.

Silicon Genetics, "Tech Notes", http:www.silicongenetics.com/cgi/MasterPFP.cgi?doc=http://www.silicongenetics.com/c..., 5 pages, downloaded Nov. 22, 2002.

NCBI LocusLink, http://www.ncbi.nlm.nih.gov/LocusLink/, downloaded Apr. 3, 2003.

NCBI Entrez Genome, http://www.ncbi.nih.gov/mapview/map_search.cgi?taxid=9606, pp. 1-2, downloaded Apr. 3, 2004.

NCBI Entrez Genome, "Homo sapiens genome data and search tips", http://www.ncbi.nlm.nih.gov/cgi-bin/Entrez/static/humansearch.html, pp. 1-30, downloaded Nov. 22, 2002.

Silicon Genetics, "Analysis, Clustering and Predictive Tools", http://www.silicongenetics.com/cgi/SiG.cgi/Products/GeneSpring/tools.smf, p. 1, downloaded Jul. 15, 2002.

Autio, et al. "CGH-Plotor: MATLAB toolbox forCGH-data analysis", Bioinformatics, vol. 19 No. 13 2003, pp. 1714-1715.

Chi, et al. "BMC Bioinformatics", SeeGH—A software tool for visualization of whole genome array comparative genomic hybridization data, http://www.biomedcentral.com/1471-2105/5/13Feb. 9, 2004, pp. 1-6.

Rao, et al. "The Table Lens: Merging Graphical and Symbolic Representations in an Interactive Focus+ Context Visualization for Tabular Information", Proceeding of the ACM SIGCHI Conference on Human Factors in Computings Systems, Bostom, MA, Apr. 1994, ACM. pp. 1-7.

Kincaid, et al. "VistaClara: An Interactive Visualization for Exploratory Analysis of DNA Microarrays", Mar. 14-17, 2004, Nicosia, Cypus. pp. 167-174.

Karp, Peter. An Ontology For Biological Function Based On Molecular Interactions. Oxford University Press. 2000. vol. 16. No. 3, pp. 269-285.

U.S. Appl. No. 11/128,896 Non-Final Office Action dated Apr. 1, 2008.

Raychaudhuri, Soumya, Chang, Jeffrey, Sutphin, Patrick and Altman, Russ, Associating Genes with Gent Ontology Codes Using a Maximum Entropy Analysis of Biomedical Literature, Cold Spring Harbor Laboratory Press, Genome Research, vol. 12, pp. 203-214, Jan. 2002.

U.S. Appl. No. 11/128,896 Non Final Office Action dated Mar. 23, 2009.

U.S. Appl. No. 10/403,762 Non Final Office Action dated Dec. 16, 2008.

Pollack, et al, Genome Wide Analysis of DNA Copy-Number Changes Using cDNA Microarrays, Nature Genetics, vol. 23. 1999 pp. 41-46.

U.S. Appl. No. 10/817,244 Non Final Office Action dated Nov. 14, 2008.

European Patent Office, Munich Germany, Nov. 26, 2007, Communication with European Search Report.

Jareborg N et al: Alfresco—a workbench for comparative genomic sequence analysis Genome Research, Cold Spring Harbor Laboratory Press, Woodbury, NY, US, vol. 10, No. 8, Aug. 2000.

Helt G A et al: "BioViews: Java-based tools for genomic data visualization" Genome Research, Cold Spring Harbor Laboratory Press, Woodbury, NY, US, vol. 8, No. 3, Mar. 1998.

Duret L et al: 'LALNVIEW: A graphical viewer for pairwise sequence aligments Cabios computer applications in the biosciences, IRL Press, Oxford, GB, vol. 12, No. 6, 1996.

* cited by examiner

US 7,825,929 B2

SYSTEMS, TOOLS AND METHODS FOR FOCUS AND CONTEXT VIEWING OF LARGE COLLECTIONS OF GRAPHS

CROSS-REFERENCE

This application is a continuation-in-part application of application Ser. No. 10/964,524, filed Oct. 12, 2004, pending, which is a continuation-in-part of application Ser. No. 10/817,244, filed Apr. 3, 2004, pending, to both of which we claim priority under 35 U.S.C. Section 120, which also claims the benefit of U.S. Provisional Application No. 60/460,479, now abandoned, and to which we also claim the benefit. application Ser. No. 10/964,524, application Ser. No. 10/817, 244 and Provisional Application No. 60/460,479 are all hereby incorporated herein, in there entireties, by reference thereto.

BACKGROUND OF THE INVENTION

The advent of new experimental technologies that support molecular biology research have resulted in an explosion of data and a rapidly increasing diversity of biological measurement data types. Examples of such biological measurement types include gene expression from DNA microarray or Taqman experiments, protein identification from mass spectrometry or gel electrophoresis, cell localization information from flow cytometry, phenotype information from clinical data or knockout experiments, genotype information from association studies and DNA microarray experiments, Comparative Genomic Hybridizaton (CGH) data, array-based CGH data (ACGH) data, etc. This data is rapidly changing. New technologies frequently generate new types of data.

As array-based CGH technology develops, studies using this technology will include ever increasing numbers of arrays from which data is generated. There is a need to visualize such data in the context of a whole study to facilitate visual exploratory analysis of the data in context. Other fields may have the same or similar needs that may be met by a solution to visualize large data sets that may individually be represented in line graph form.

Current techniques for visualizing data typically do not scale well to large numbers of arrays, or do not visualize sufficient detail regarding an individual array when the technique is scalable to display data from a large number of arrays. For example, standard heat map-type visualizations may be employed to represent aCGH data, for example, see Pollack et al, "Microarray analysis reveals a major direct role of DNA copy number alteration in the transcriptional program of human breast tumors", PNAS, Oct. 1, 2002, vol. 99, no. 20, 12963-12968, which is incorporated herein, in its entirety, by reference thereto. While such representations are generally scalable to large numbers of arrays/experiments, it is difficult to explore the details underlying the heat maps. Other software products that share the same limitations include "dchip", see http://www.dchip.org, BioConductor, see http://www.bioconductor.org, and GeneSpring, see http://www.silicongenetics.com.

Visualization software and systems that are adapted specifically to CGH visualizations tend to show data superimposed on chromosome ideograms, see, for example, currently pending application Ser. No. 10/817,244 filed Apr. 3, 2004 and titled "Visualizing Expression Data on Chromosomal Graphic Schemes" and co-pending application Ser. No. 10/964,524 filed Oct. 12, 2004 and titled "Systems and Methods for Statistically Analyzing Apparent CGH Data Anomalies and Plotting Same", both of which are hereby incorporated herein, in their entireties, by reference thereto. While this is a natural context for CGH studies, such representations do not scale well for visualizing hundred of experiments simultaneously on a display, for example.

Visualization software and systems for displaying sparse data contained within very large datasets are described in co-pending application Ser. No. 10/918,897 filed Aug. 13, 2004 and titled "System and Methods for Navigating and Visualizing Multi-Dimensional Data", which is incorporated herein, in its entirety, by reference thereto.

There is a continuing need for methods, tools and systems that facilitate the visualization of larger collections of data, such as data that may be represented as groups of line graphs, in a compact graphical form.

SUMMARY OF THE INVENTION

Systems, tools, methods and computer readable media for visualizing a collection of graphs to provide context and focus are provided, wherein each of the graphs may be aligned along a first axis of a visualization. A compressed visualization is formed by compressing all of the graphs in a direction along a second axis of the visualization that is perpendicular to the first axis. At least one of the compressed graphs may be zoomed to make a visualization of the at least one graph having a greater scale along the second axis than a scale of the compressed graphs. The at least one zoom graph may be displayed along with the compressed graphs, wherein the at least one zoomed graphs are displayed in a same order relative to the compressed graphs and each other as occupied prior to the zooming.

A user interface for use in visualizing a collection of graphs in an overall view while at the same time providing the ability to view detail with regard to at least one of the graphs is provided, including: a display configured to visualize the collection of graphs in compressed form; a feature for selecting a graph from the visualization of the compressed collection, wherein upon selecting a graph, said interface zooms at least the selected graph to make a visualization of at least the selected graph having a greater scale along an axis of compression of the compressed visualization than a scale of the compressed graphs along the axis of compression; and wherein at least the selected graph is displayed in a same order as occupied in the compressed form, with graphs not having been zoomed being displayed adjacent zoomed graphs.

These and other advantages and features of the invention will become apparent to those persons skilled in the art upon reading the details of the methods, tools, systems and computer readable media as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
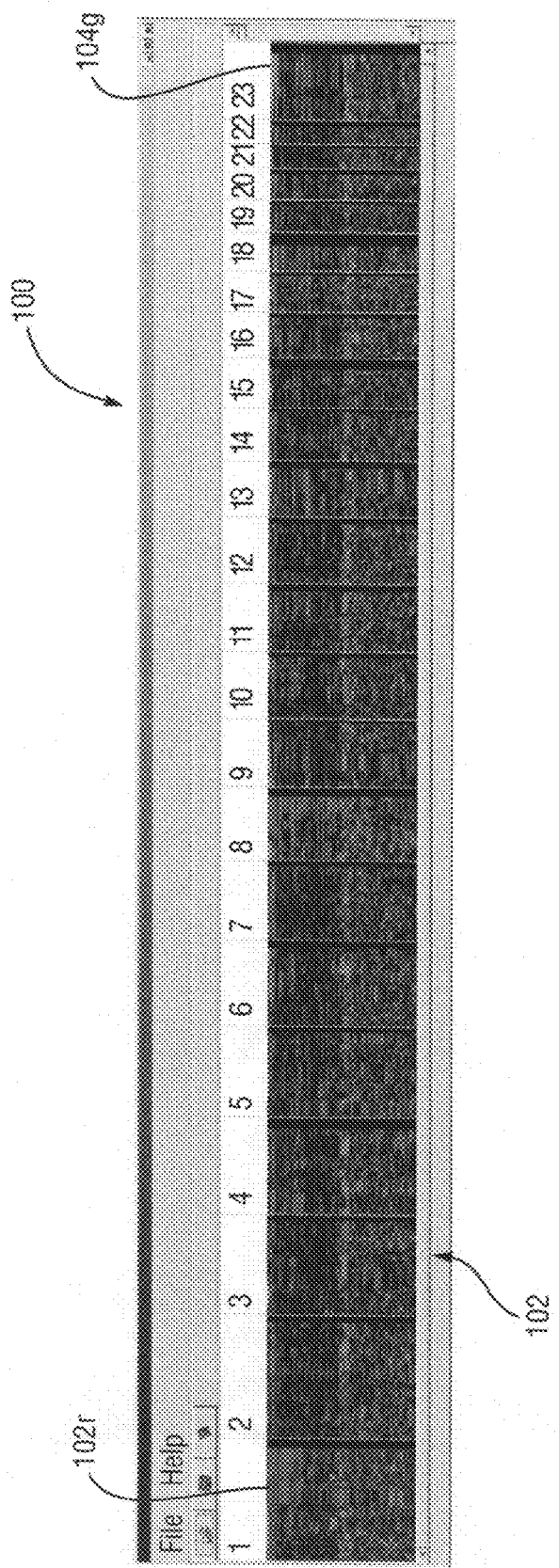
FIG. 1 shows a display of compressed line graphs, as visualized on a user interface.

Before the present methods, tools, systems and computer readable media are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a graph" includes a plurality of such graphs and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

An "aberrant region" refers to an uninterrupted section of genetic data on a chromosome which has been identified to show significant amplification or deletion of genetic material.

"Color coding" refers to a software technique which maps a numerical or categorical value to a color value, for example representing high levels of gene expression or gene amplification as a reddish color and low levels of gene expression or a level of gene deletion as greenish colors, with varying shade/intensities of these colors representing varying degrees of expression or amplification. Intermediate colors may also be used. For example, genetic material which has been neither deleted nor amplified may be represented by a third color, such as black. Color-coding is not limited in application to expression levels or CGH data, but can be used to differentiate any data that can be quantified, so as to distinguish relatively high quantity values from relatively low quantity values. In any of these cases, a third color can be employed for relatively neutral or median values, and shading can be employed to provide a more continuous spectrum of the color indicators.

A "heat map" or "heat map visualization" is a visual representation of data wherein color-codings are used for displaying numerical values or ranges of numerical values. Numerical values or ranges of numerical values in a line graph may be encoded into colors representative of those numerical values or ranges, respectively. Color encodings may run on a continuum from one color through another, e.g. green to red or yellow to blue for numerical values.

The term "down-regulation" is used in the context of gene expression, and refers to a decrease in the amount of messenger RNA (mRNA) formed by expression of a gene, with respect to a control.

The term "gene" refers to a unit of hereditary information, which is a portion of DNA containing information required to determine a protein's amino acid sequence.

"Gene expression" refers to the level to which a gene is transcribed to form messenger RNA molecules, prior to protein synthesis.

"Gene expression ratio" is a relative measurement of gene expression, wherein the expression level of a test sample is compared to the expression level of a reference sample.

A "gene product" is a biological entity that can be formed from a gene, e.g. a messenger RNA or a protein.

"CGH data" refers to data obtained from "Comparative Genomic Hybridization" measurements. CGH involves a technique that measures DNA gains or losses. Some techniques perform this at the chromosomal level, while newer emerging techniques, such as "array CGH" (aCGH) use high throughput microarray measurements to measure the levels of specific DNA sequences in the genome. While not specifically limited to aCGH data, the present invention is applicable to aCGH data, which comes in a form analogous to array-based gene expression measurements.

The term "promote" refers to an increase of the effects of a biological agent or a biological process.

A "protein" is a large polymer having one or more sequences of amino acid subunits joined by peptide bonds.

The term "protein abundance" refers to a measure of the amount of protein in a sample; often done as a relative abundance measure vs. a reference sample.

"Protein/DNA interaction" refers to a biological process wherein a protein regulates the expression of a gene, commonly by binding to promoter or inhibitor regions.

"Protein/Protein interaction" refers to a biological process whereby two or more proteins bind together and form complexes.

A "sequence" refers to an ordered set of amino acids forming a protein or to an ordered set of nucleic acid bases forming a DNA fragment or an RNA molecule.

The term "overlay" or "data overlay" refers to a user interface technique for superimposing data from one view upon data in a different view; for example, overlaying gene expression ratios on top of a chromosome view.

A "spreadsheet" is an outsize ledger sheet simulated electronically by a computer software application; used frequently to represent tabular data structures.

The term "up-regulation", when used to describe gene expression, refers to an increase in the amount of messenger RNA (mRNA) formed by expression of a gene, with respect to a control.

The term "view" refers to a graphical presentation of a single visual perspective on a data set.

The term "visualization" or "information visualization" refers to an approach to exploratory data analysis that employs a variety of techniques which utilize human perception; techniques which may include graphical presentation of large amounts of data and facilities for interactively manipulating and exploring the data.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other nucleic acids that are C-glycosides of a purine or pyrimidine base, polypeptides (proteins) or polysaccharides (starches, or polysugars), as well as other chemical entities that contain repeating units of like chemical structure.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "functionalization" as used herein relates to modification of a solid substrate to provide a plurality of functional groups on the substrate surface. By a "functionalized surface" is meant a substrate surface that has been modified so that a plurality of functional groups are present thereon.

The terms "reactive site", "reactive functional group" or "reactive group" refer to moieties on a monomer, polymer or substrate surface that may be used as the starting point in a synthetic organic process. This is contrasted to "inert" hydrophilic groups that could also be present on a substrate surface, e.g., hydrophilic sites associated with polyethylene glycol, a polyamide or the like.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "oligonucleotide bound to a surface of a solid support" refers to an oligonucleotide or mimetic thereof, e.g., PNA, that is immobilized on a surface of a solid substrate in a feature or spot, where the substrate can have a variety of configurations, e.g., a sheet, bead, or other structure. In certain embodiments, the collections of features of oligonucleotides employed herein are present on a surface of the same planar support, e.g., in the form of an array.

The term "array" encompasses the term "microarray" and refers to an ordered array presented for binding to nucleic acids and the like. Arrays, as described in greater detail below, are generally made up of a plurality of distinct or different features. The term "feature" is used interchangeably herein with the terms: "features," "feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids.

An "array," includes any one-dimensional, two-dimensional or substantially two-dimensional (as well as a three-dimensional) arrangement of addressable regions (i.e., features, e.g., in the form of spots) bearing nucleic acids, particularly oligonucleotides or synthetic mimetics thereof (i.e., the oligonucleotides defined above), and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either nucleic acid precursor units (such as monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

In certain embodiments of particular interest, in situ prepared arrays are employed. In situ prepared oligonucleotide arrays, e.g., nucleic acid arrays, may be characterized by having surface properties of the substrate that differ significantly between the feature and inter-feature areas. Specifically, such arrays may have high surface energy, hydrophilic features and hydrophobic, low surface energy hydrophobic interfeature regions. Whether a given region, e.g., feature or interfeature region, of a substrate has a high or low surface energy can be readily determined by determining the regions "contact angle" with water, as known in the art and further described in co-pending application Ser. No. 10/449,838, the disclosure of which is herein incorporated by reference. Other features of in situ prepared arrays that make such array formats of particular interest in certain embodiments of the present invention include, but are not limited to: feature density, oligonucleotide density within each feature, feature uniformity, low intra-feature background, low inter-feature background, e.g., due to hydrophobic interfeature regions, fidelity of oligonucleotide elements making up the individual features, array/feature reproducibility, and the like. The above benefits of in situ produced arrays assist in maintaining adequate sensitivity while operating under stringency conditions required to accommodate highly complex samples.

An array is "addressable" when it has multiple regions of different moieties, i.e., features (e.g., each made up of different oligonucleotide sequences) such that a region (i.e., a "feature" or "spot" of the array) at a particular predetermined location (i.e., an "address") on the array will detect a particular solution phase nucleic acid sequence. Array features are typically, but need not be, separated by intervening spaces.

Any given substrate may carry one, two, four or more arrays disposed on a front surface of the substrate and depending on the use of the array, any or all of the arrays may be the same or different from one another and each may contain multiple spots or features. The one or more arrays usually cover only a portion of the surface, with regions of the surface adjacent the opposed sides and leading end and trailing end of the surface not being covered by any array. Each array can be designed for testing against any type of sample, whether a trial sample, reference sample, a combination of them, or a known mixture of biopolymers such as polynucleotides. The substrate may be of any shape, as mentioned above.

As mentioned above, an array contains multiple spots or features of oligomers, e.g., in the form of polynucleotides, and specifically oligonucleotides. As mentioned above, all of the features may be different, or some or all could be the same. The interfeature areas may be of various sizes and configurations. Each feature carries a predetermined oligomer such as a predetermined polynucleotide (which includes the possibility of mixtures of polynucleotides). It will be understood that there may be a linker molecule of any known types between the surface and the first nucleotide.

The substrate may carry an identification code, e.g., in the form of a bar code or the like printed on the substrate in the form of a label attached by adhesive or any convenient means. The identification code may contain information relating to the array(s) located on the substrate, where such information may include, but is not limited to, an identification of array(s), i.e., layout information relating to the array(s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

Sensitivity is a term used to refer to the ability of a given assay to detect a given analyte in a sample, e.g., a nucleic acid species of interest. For example, an assay has high sensitivity if it can detect a small concentration of analyte molecules in sample. Conversely, a given assay has low sensitivity if it only detects a large concentration of analyte molecules (i.e., specific solution phase nucleic acids of interest) in sample. A given assay's sensitivity is dependent on a number of parameters, including specificity of the reagents employed (e.g., types of labels, types of binding molecules, etc.), assay conditions employed, detection protocols employed, and the like. In the context of array hybridization assays, such as those of the present invention, sensitivity of a given assay may be dependent upon one or more of: the nature of the surface immobilized nucleic acids, the nature of the hybridization and wash conditions, the nature of the labeling system, the nature of the detection system, etc.

Liquid chromatography is an analytical chromatographic technique that is useful for separating components, typically ions or molecules, that are dissolved in a solvent. In this technique, the components (e.g., analytes) are first dissolved in a solvent and then are forced to flow through a chromatographic column that can range from a few centimeters to several meters. The column is packed with a solid phase chromatographic material that is matched to the solvents in use and binds the analytes via adsorption. An additional, different solvent is then mixed into the flow in increasing concentrations (such as by a smooth gradient increases, or step-wise increases, for example). Each compound in the analyte releases from the solid phase at a specific concentration of the additional solvent and then flows off of the column resulting in a serial separation of the compounds contained in the analyte. A variety of detectors for identifying the presence of compounds in the effluent have been developed over the past thirty years based on a variety of different sensing principles. Typically, signal intensity from a chromatographic detector can be plotted as a function of elution time (a chromatogram) and peaks are used to identify the components. Other techniques, such as characteristic retention time in a chromatographic column, may also be applied to identify the components. A mass spectrometer in this application functions as a very sensitive, multiplexed detector that can detect the presence of multiple compounds simultaneously and can differentiate between the compounds detected.

Liquid chromatography/mass spectrometry (LC/MS) is a widely used technique for the global identification and quantitation of proteins, peptides and/or metabolites in complex biological samples. In this technique, liquid chromatography is used in-line with a mass spectrometer to chromatographically separate components prior to mass detection, in order to reduce the number of components presented to the mass spectrometer at a given time.

The present invention provides systems, tools methods and computer readable media for visualizing very large collections of line graphs, scatter plots or any other data that can be converted into line graph representations, in a compact, graphical form, while still maintaining the ability to examine a single, or several such line graphs in detail, in the context of the very large collection of graphs. Such abilities are sometimes referred to as context and focus. For example, when compressing scatter plots, the points in the scatter plots may be connected by gradient lines each connecting two points. These could be linear gradients or gradients that represent a spline fit or any other interpolation scheme. If multiple points of a plot exist on the same X-axis location, then those values may be averaged or otherwise combined into one representative data value per X-axis location, because in the most collapsed or compressed view, each X-coordinate location point can only be represented by one Y-Coordinate value. Also, when fully compressed, the view is essentially a heat map view, where Y-coordinate values may be represented by color-coding. Examples of data that may be displayed and manipulated according to the present invention include, but are not limited to: collections of aCGH data provided from experiments carried out on arrays (e.g., hundreds up to thousands of such experiments may be displayed on a single display, such as a computer monitor display); or collections of related spectra such as a collection of ultraviolet spectra, a collection of visual light spectra, a collection of infrared spectra, a collection of nuclear magnetic resonance spectra, a collection of mass spectrographs, or any other collection of related spectra, or any other data that can be represented in line graph form. Exploration in detail of data within displays of such collections is also possible.

Referring now to FIG. 1, an example of a display 100 produced by the present system is shown in fully compressed form. In fully compressed form, display 100 resembles some visualizations that are currently made for displaying aCGH data. The data displayed in FIG. 1 is from a breast cancer study conducted by Pollack et al. and reported in "Microarray analysis reveals a major direct role of DNA copy number alteration in the transcriptional program of human breast tumors", which as incorporated by reference above. In the view shown, data from a collection of eighty-two microarray experiments is displayed in compressed form. The view 100 is shown in scale so that it can be understood that hundreds or even thousands of such experiments could be displayed on a standard computer display in a single visualization. Further, if additional experiments exist (i.e., greater than a maximum number that can be displayed at one time on the visualization), the user interface is equipped to scroll through the display to visualize the additional experiments.

Data for eighty-two microarrays (some gene expression and some aCGH) were loaded into the system and a simple moving average was computed for every contiguous group of twenty measurements for a single array. Contiguous measurements are those measurements taken from contiguous locations along a chromosome, and the data from the same is displayed in the same order, relative to chromosome position. A color-gradient mapping of ratio values (between cancer and non-cancer samples) is displayed wherein, for example, ratios less than a value of one may be color-coded by a first color and ratio values greater than one may be color-coded by a second color. Additionally, ratio values equal to one may be color-coded by a third color. For example, a continuous, nonlinear, sigmoidal color grading schema may be employed where low ratios much less than one are assigned a bright green color, with the green color continuously darkening as values approach one, with values of one assigned a black color, and with values greater than one being assigned a red color, dark red for values only slightly greater than one and increasingly and continuously brightening as the values increase. For CGH values that are plotted, the user may interpret high ratios as possible amplifications and low ratios as possible deletions. Alternatively, Z-scores or other statistical aberrations scores may be plotted with regard to the CGH data and then plotted as described herein. An example of such Z-score plotting is described in application Ser. No. 10/964, 524 and then plotted as described herein.

To make the most compact possible rendering of the data, each line segment of each line graph representing the microarrays was color-coded (e.g., in the same or similar way that heat map coloring is done in typical gene expression heat maps). For an example of typical heat map color coding, see Kincaid, "VistaClara: an interactive visualization for exploratory analysis of DNA microarrays", Proceedings of the 2004 ACM symposium on Applied computing, ACM Press, 2004, pp 167-174, and co-pending application Ser. No. 10/403,762 filed Mar. 31, 2003 and titled "Methods and System for Simultaneous Visualization and Manipulation of Multiple Data Types", both of which are hereby incorporated herein, in their entireties, by reference thereto. Color-coding allows the graphic representation of the line graphs in compressed form, such that regions of interest, such as deletions and amplifications (and/or significant increases and decreases in expression levels) may still be noticed by the color representations thereof, albeit in much less detail. However, such a compressed view may be very powerful for visual identification of trends among multiple experiments. For example, in FIG. 1, it can be seen that many of the experiments show amplification in the region of chromosome 1 identified by 102r in FIG. 1, as indicated by the large block(s) of red color-coding. An example of multiple arrays showing deletion can be observed at chromosome 23, see reference numeral 104g.

Figure 2:
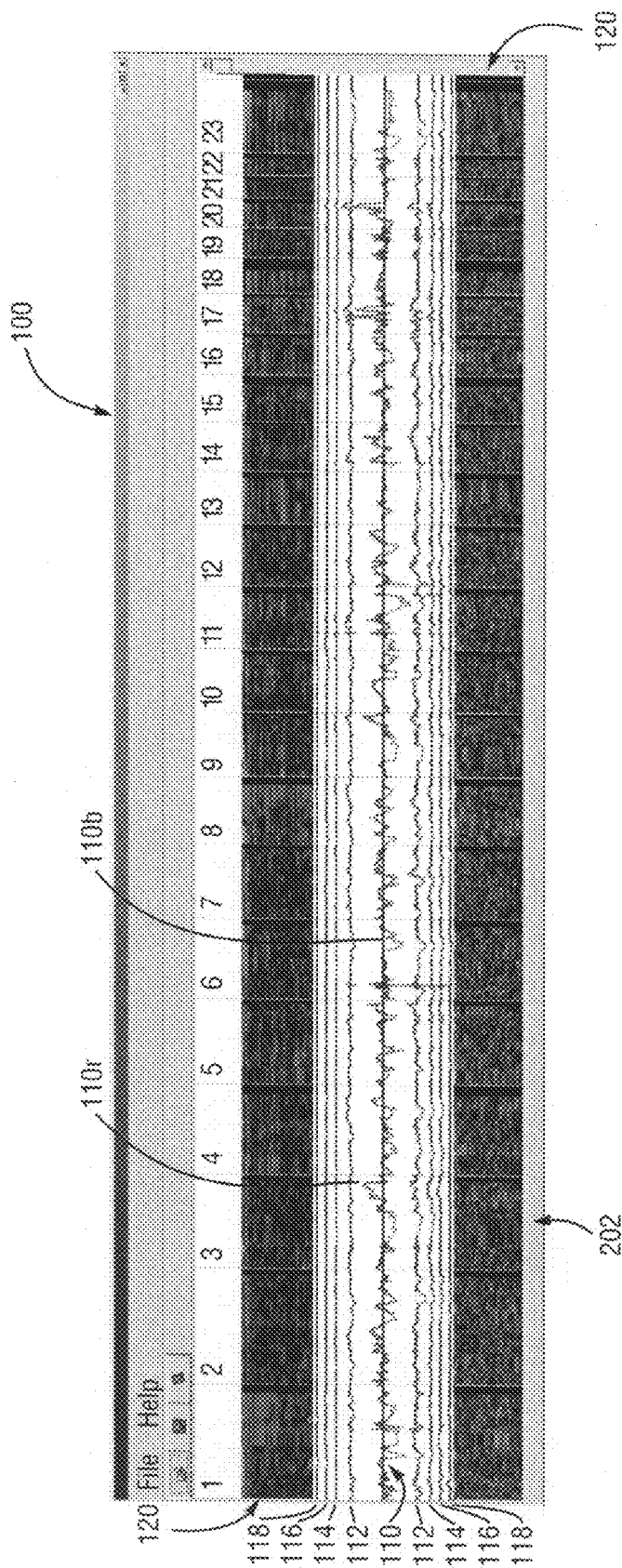
FIG. 2 shows a display of the visualization shown in FIG. 1, wherein a selected portion of the compressed display has been decompressed, expanded, or zoomed with respect to a first direction along a first axis to visualize greater detail with regard to the selected portion.

Although a compressed view such as shown in FIG. 1 may be useful for identifying trends among multiple experiments, as described above, such a visualization does not show detail about the individual graphs that are compressed therein, as each graph is compressed to a scale (vertical scale or height, in FIG. 1, but may alternatively be a horizontal scale, width) of only about one to two pixels per graph, so that variations in magnitude along the scale are not visible in the compressed format. Thus, one viewing a compressed visualization, such as the visualization in the form shown in FIG. 1, cannot discern very much detail about the behavior across any particular array or chromosome. The present system improves the versatility of such a display by providing the capability to zoom or expand a selected portion of a compressed visualization. For example, by "clicking on" or otherwise selecting a region of interest in the display of FIG. 1, that region is decompressed, expanded, or zoomed open to a visual representation of the data as shown in FIG. 2.

The location clicked on is expanded to the most zoomed or magnified representation in the display. That is, the line graph 110 selected by or nearest to the selection on the visualization 102 is the line graph that is displayed the largest in the expanded visualization 202 shown in FIG. 2. Not only does the system magnify or zoom the selected line graph 110, but neighboring line graphs 112 are displayed in magnified view as well, although at a lesser vertical magnification or scale than what line graph 110 is displayed at. In the example shown, line graphs 112, 114, 116 and 118 are displayed in progressively decreasing smaller vertical scale, relative to the vertical scale of line graph 110 to communicate the visual impression of the transition from the zoomed line graph 110 down to the fully compressed line graphs 120. Although useful, it is noted that displaying the zoomed line graphs in progressively decreasing vertical scale in both directions away from the largest-zoomed line graph 110 is not necessary to the invention, as other display schemes may be alternatively employed. For example, line graphs 112, 114, 116 and 118 may all be displayed in the same vertical scale, although a smaller vertical scale than that which line graph 110 is displayed in. Or more or fewer line graphs may be displayed in a zoomed scale adjacent line graph 110. Or line graphs may be expanded adjacent only one side of the selected line graph 110 (either above or below). Of course there are many other display schemes that may be employed alternatively to those listed, as would be readily apparent to one of ordinary skill in the art.

By displaying neighboring line graphs 112, 114, 116, 118 in a zoomed scale (whether the same scale as line graph 110, decreasingly smaller vertical scales in directions away from line graph 110, or some other display scheme) a viewer is provided the opportunity to view details of the immediate neighborhood of the selected experiment (e.g., line graph 110). Thus this feature is useful to compare details of neighboring line graphs/experimental results. This feature is further useful to correct slight navigation errors. That is, when in the fully compressed form 102, the user may make a selection error among the rows in compressed form. For example, in the example shown in FIGS. 1-2, the user may have actually had the most interest in viewing the details of the line graph 114 that is shown displayed above line graph 110 in FIG. 2. In this case, when presented with the visualization of FIG. 2, the user may simply click on or otherwise select line graph 114 that was originally intended to be selected for closer observation. The system then redisplays the line graphs to have a visualization similar to that shown in FIG. 2, but where the line graph 114 shown above line graph 110 in FIG. 2 is now displayed to have the largest vertical scale, with line graphs 112, 110, 112 and 114 displayed in decreasingly smaller vertical scale below line graph 114, and line graphs 116, 118 and two other line graphs immediately above line graph 118, but unlabeled in FIG. 2, displayed in decreasingly smaller vertical scale.

Referring again to FIG. 2, it is noted that the heat map coloring of the enlarged line graphs 110, 112, 114, 116 and 118 is maintained as a visual cue, to assist a viewer in associating high values of the expanded line graphs with the same color regions in the compressed graphs, and low values of the expanded line graphs with the same color regions in the compressed graphs, respectively. For example, segment 110*r* of line graph 110 is color coded red to indicate amplification or increases in expression levels, even though, in the zoomed view shown, this can also readily be appreciated by the fact that segment 110*r* is above the baseline 110*b*. Similarly, segment 110*g* is color-coded green to show deletion or decreased expression. Baseline 110*b* also indicates the row/line graph that was the selected row upon which the zooming scheme was based for the visualization.

Figure 3:
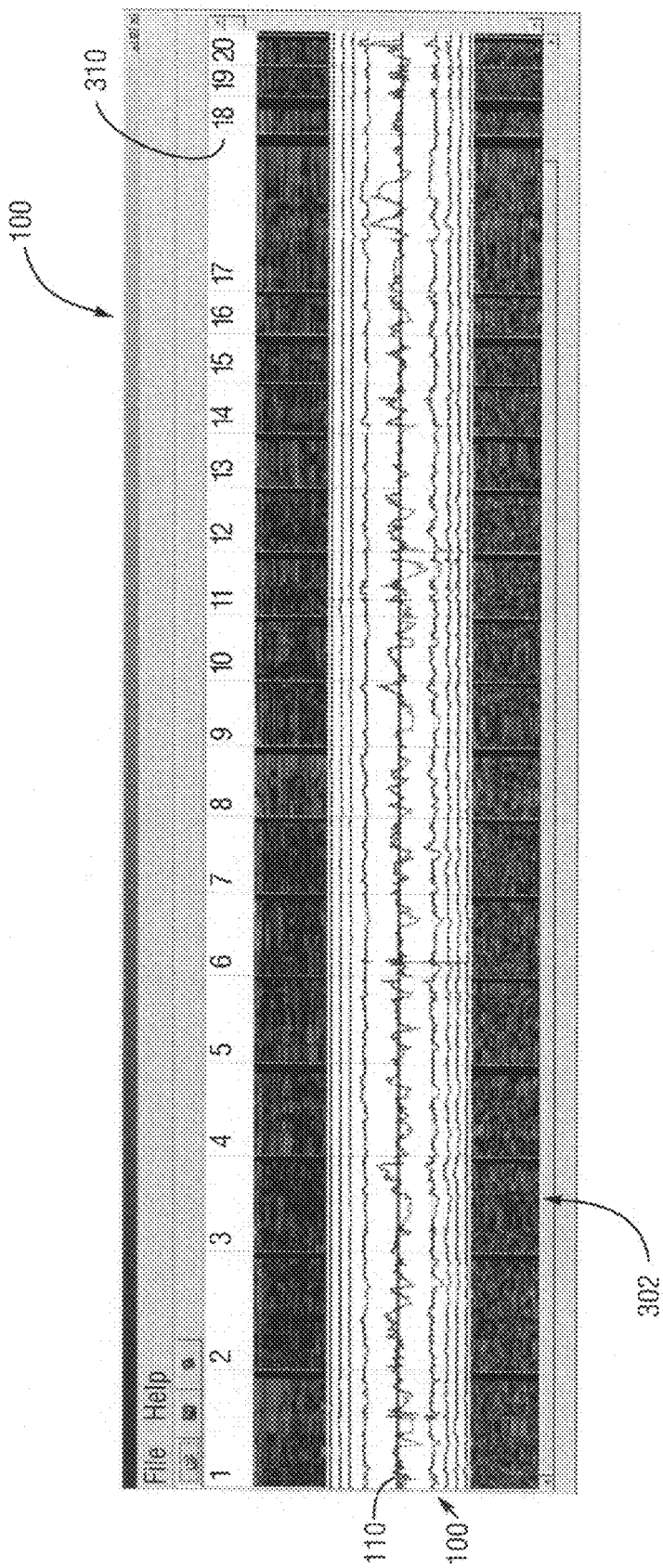
FIG. 3 shows a visualization similar to that of FIG. 2, but wherein a selected portion has further been expanded along the other axis of the visualization.

A further level of detail is accessible by clicking on or otherwise selecting the same line graph 110 a second time. That is, while the selected line graph 110 is in the zoomed view shown in FIG. 2, a user may then click or otherwise select on a region of line graph 110 that the user want to expand horizontally. In response the horizontal scale of the visualization is enlarged in the region of graph 110 that was selected by the user. The region that is expanded is typically a predefined column of the visualization, which may represent a chromosome, for example, or other predefined region or measurement. In the example shown, consider that the user selected line graph 110 in the column identified by the number 17 (referring to chromosome 17). In FIG. 2, the data that corresponds to chromosome 17 is displayed along a much shorter length than what is displayed relative to some of the other chromosomes (e.g., 1, 2, 3, etc.) By clicking on line graph 110 in the chromosome 17 (column 17) region, the data under chromosome 17 is expanded as shown in FIG. 3, so that the visualization 302 shows details of the line graphs, in regions corresponding to chromosome 17 can be more readily discerned, as the length of column 17 have been increased, thereby enlarging the horizontal scale of the data under chromosome 17 with respect to all line graphs.

Figure 4:
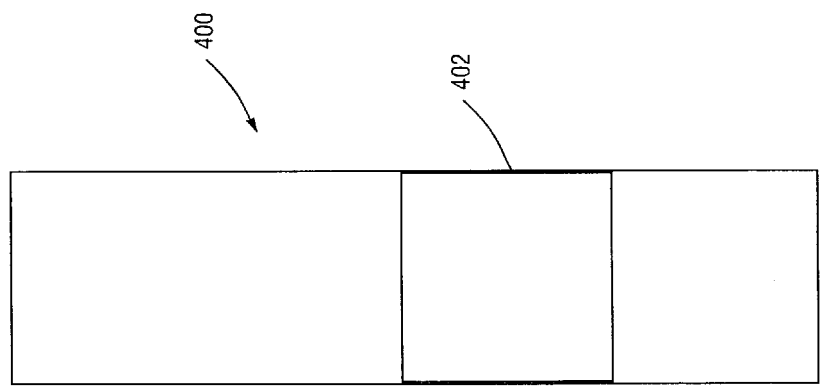
FIG. 4 schematically shows a scroll tool that may be used during visual scanning of detailed graphs in a collection of graphs.

An alternative to clicking on a different line graph to change the focus of zooming, i.e., to select a different line graph that is to be enlarged by the greatest vertical scale, the system allows scrolling of the visualization. A scroll bar 400 (see FIG. 4) or other feature or tool may be provided for interactive use by a user to change the selection of a line graph to be magnified, by scrolling to the line graph to be selected. By dragging button 402 vertically either upwardly or downwardly, base line 110*b* acts as a cursor and moves vertically, either upwardly or downwardly over the line graphs in the visualization, wherein the movements of base line 110*b* correspond to the movements of button 402 by the user. As each line graph is passed over by baseline 110*b* during the scrolling, it is magnified or zoomed to an enlarged graph such as like what is shown by graph 110 in FIG. 2. Additionally, adjacent graphs may also be enlarged during the scrolling, to the extent shown in FIG. 2, for example. In this sense, scrolling gives a visual effect somewhat like sliding a magnification bar (e.g., a rectangular magnifying glass for reading small text) over the graphs, wherein the graph at the center of the "magnification bar", i.e., defined by what baseline 110*b* overlies is magnified to the greatest extent. By "dropping" button 402 in a selected location, the corresponding line graph that base line 110*b* overlies is selected and displayed in an enlarged visualization as shown and described with respect to line graph 110, FIG. 2. As noted, the scrolling feature may be further advantageous as zooming of each line graph that baseline 110*b* passes over may occur as baseline 110*b* is passing over it. In this way, the user is provided with a rapid, "scanning" ability of the details of the data, which may be useful in making a decision as to which line graph to select to provide a zoomed visualization for further detailed observation. Further such scrolling may be used to further identify trends and similarities and/or differences among the graphs.

An alternative feature for resizing a horizontal scale of data of interest enables the user to click on or select (e.g., drag and drop) one or more column separators 310 of the visualization. For example, by dragging and dropping separator 310 in FIG. 3, the user can accomplish the same view as resulted from clicking on line graph 110 a second time in the region underlying chromosome 17, as described above. However, this feature provides more versatility, as the user may drag and drop one or more separators and may also vary the distances by which one or more columns are horizontally expanded. For example, the user may want the information under chromosome 17 in FIG. 3 to be shown in even greater detail, in which case, the user could drag separator 310 still further to the right to drop it into a new, further expanded location. Or the data under chromosome 17 could have been horizontally expanded somewhat, but less than is shown in FIG. 3, by dropping separator 310 at a position to the left of where it is shown in FIG. 3. Still further, more than one region may be horizontally expanded by moving one or both separators 310 defining a region to be expanded.

For data that is plotted by calculation of moving averages, the system provides the ability of re-computing moving averages such that the computations are based on a different window size than that computed under a default window size. For example, the data displayed in FIG. 1 was displayed based on moving averages calculated for every contiguous group of twenty measurements. The user may decide to decrease or increase the window size, and then visualize the data based upon moving averages computed using the new window size. For example, the user may instruct the system to re-display the data based upon computations of moving averages calculated for every contiguous group of fifteen measurements, or for every contiguous group of thirty measurements.

Another feature enables the user to visualize scatter plots, wherein the individual data points are plotted. Further, the individual points may be plotted on the same axis as the line graph to provide a combined visualization of the scatter plot of the individual points along with the line graph generated by the moving average values. More generally, the collapsed or compressed view of a line graph essentially reduces a two dimensional chart to a one-dimensional heat-map view (i.e., straight line with color-coded locations to represent values in the second dimension not shown in the collapsed view). When a collapsed plot is "opened" or "de-compressed" to show a two-dimensional plot, any other type of data that a user may want to associate with such plot can also be displayed as an overlay, juxtaposed with the two-dimensional line graph.

Alternative to, or in addition to plotting the line graphs (and/or scatter plots), the present system may compute values on a different basis and plot these values alone, or superimposed on a visualization of the original line graphs and/or scatter plots. Additional information to be displayed may include, but is not limited to, Z-scores, p-values, or other values calculated from the raw data.

As noted above, the present invention is not limited to aCGH data or other data from microarrays, but may be used to display any collection of data that can be represented as an ordered graph and viewed in such order. However, all graphs in the collection must be capable of being aligned along one axis (typically the horizontal axis) in a meaningful way. In the example described with regard to FIG. 1, chromosome position is common among all arrays (line graphs) visualized.

Further, it is possible to represent values continuously between points, even if the data plotted is a scatter plot or other discontinuous plot, by interpolating color gradients using straight lines, splines, or other interpolation techniques, as discussed above. This characteristic is useful so that the compressed visualization 102 fills properly when compressed. For example, the system may interpolate between adjacent data values of a scatter plot to determine a compressed value to which a color will be assigned based on the interpolated value. Thus, rather than a blank that exists between discrete points, if the blank is the representative point to be displayed in the compressed view, the system computes a value representing a value that would exist in a line graph representing the discrete data points. However, this requirement is not strictly necessary, such as in instances where a meaningful color mapping (color coding) can be established for missing areas of the heat map. For example, a discontinuous line graph that has one or more discontinuities from missing data may be rendered with a color-coding of grey or some other distinct color indicating that no data is present in that area, rather than interpolating over the missing data area to give some shade of red or green, as it is more accurate to not consider areas where the data is missing. Another example occurs with CGH data where, over the location of the centromere no data will be obtained, and this can be color-coded to indicate the lack of data. In either case, it is important to produce sufficiently visible features in the compressed map, for the reasons provided above. Such a compressed map will allow a user to identify trends, similarities and differences among the many members (experiments, graphs) that are compressed in the view.

Figure 5A:
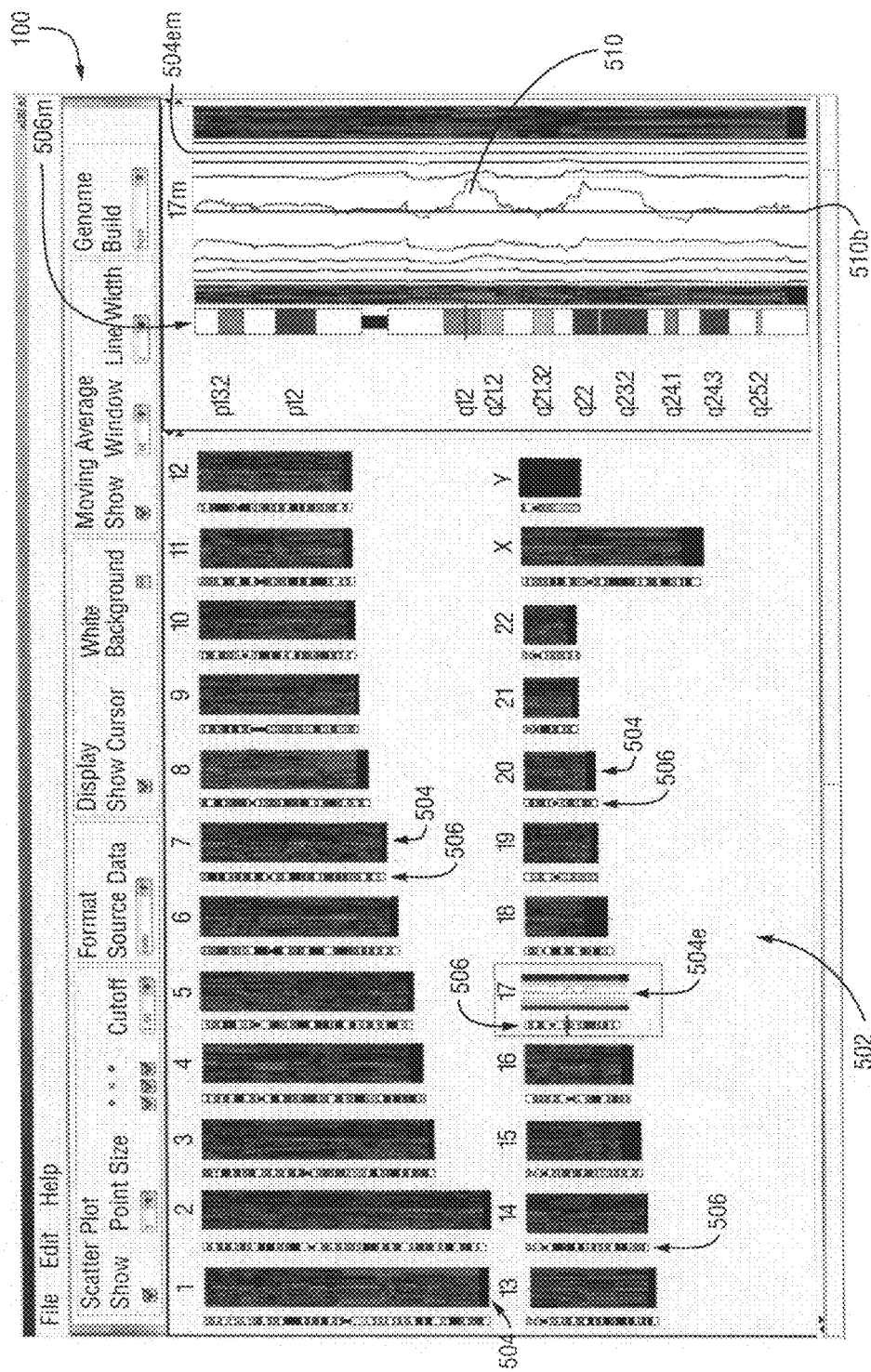
FIG. 5A shows another visual display of a collection of graphs, in which portions of the graphs are shown individually adjacent corresponding chromosome graphs.

It should be further noted here that while position (e.g., position on the chromosome) is shown in the x-axis, and experiment (e.g., microarray) has been shown along the y-axis, that clearly the axes could be reversed and still provide the same functionality, as would be readily apparent to those of ordinary skill in the art. One such example of this is shown in FIG. 5A, wherein, in addition to reversing the axes along which information is plotted, the visualizations are further individualized, or separated, and displayed on a per-chromosome basis. Thus, each visualization 504 of overall visualization 502, corresponds to a column/chromosome of the data displayed in visualization 102, after having reversed the axes along which the data is plotted. Of course, chromosome plots may be displayed horizontally such that the data is plotted in the same way it is plotted in visualization 102, as an alternative way of displaying separate chromosome visualizations. Compressed data displays 504 are displayed adjacent graphical representations 506 of the chromosomes adjacent locations where genetic material represented by the data is located on that chromosome. Further detailed information regarding visualization of chromosomes and related data on a per chromosome basis is contained in application Ser. Nos. 10/817,244 and 10/964,524, which were incorporated by reference above.

A user may select on any of the individual visualizations 506, 504, such as by clicking on a specific area within a visualization 504, for example. This interactive action prompts the system to display the selected visualization in a magnified view 506*m*, 504*m*. In the example shown in FIG. 5A, the visualization of chromosome 17 and the associated data have been selected and are displayed in a magnified view 17*m*, as a magnified chromosome map 506*m* and a magnified view of the data 504*em* that shows the selected graph in a magnified view, with adjacent graphs being displayed in magnified views, but with decreasing horizontal magnitude as one views in either direction toward the compressed graphs. The selected visualization 504 may be zoomed along the selected graph, as well as enlarging adjacent graphs in any of the manners described above. Of course, the selected graph runs vertically in this example, and the amplitudes of the graph values are expanded horizontally because of the reversal of axes along which the data was plotted.

Figure 5B:
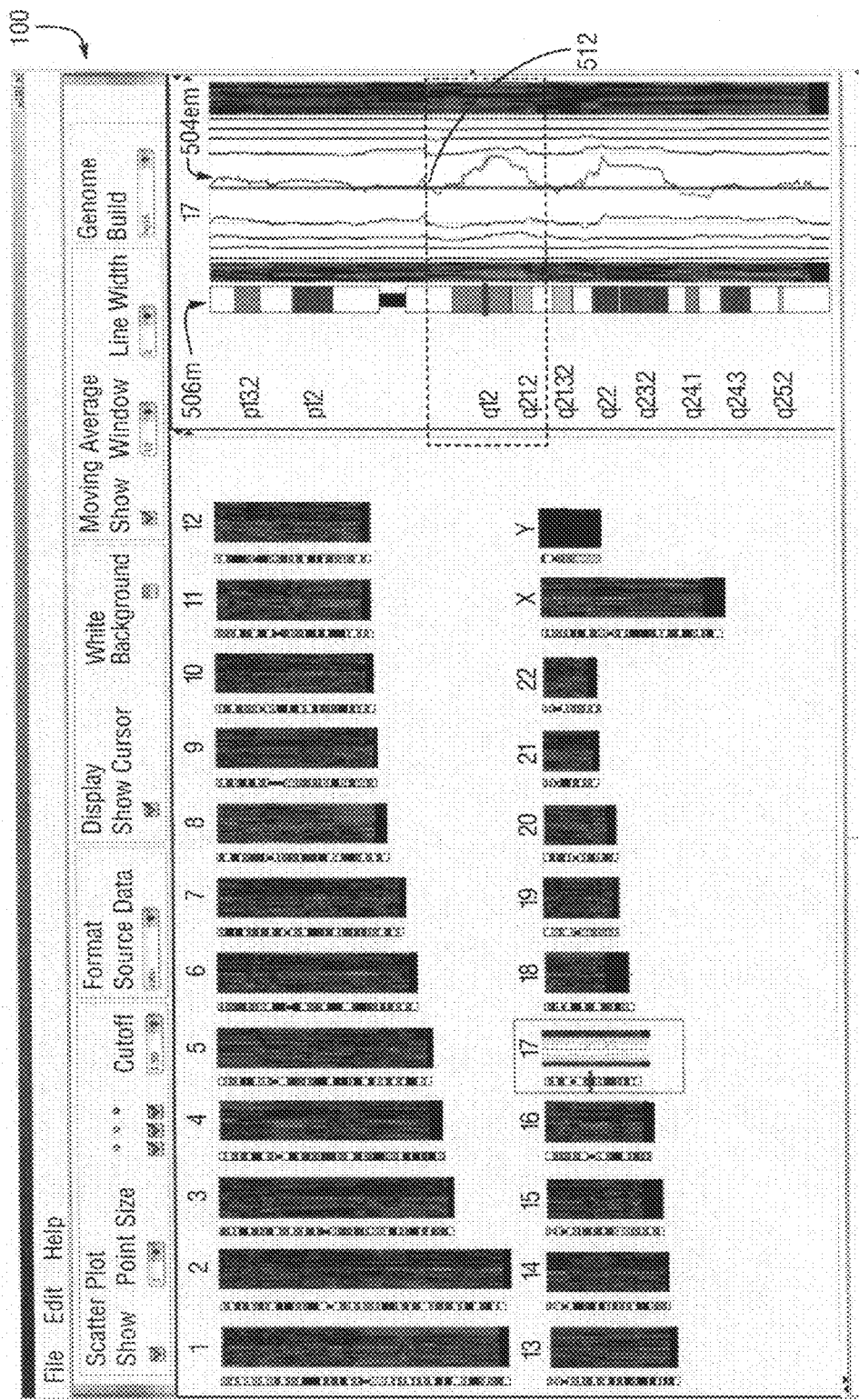
FIG. 5B is another view of the graphs shown in FIG. 5A, but wherein a vertical expansion of the graphs shown in the expanded view have been further vertically expanded about a selected region.

The enlarged visualization is also interactive, so that the user may select another graph to view in the greatest magnification, by clicking on that graph, or by scrolling though graphs in a manner as described previously. As view 504*em* is modified according the user's selections, view 504*e* is modified in the same way. A second selection of a selected graph (i.e. a selection on a portion of a graph already displayed at the largest magnitude) 510 may expand the scale of that portion of the graph in a vertical direction to show more detail along that portion of the graph wherein the corresponding graph 506*m* of the associated chromosome expands by the same amount to show greater detail on the chromosome map. FIG. 5B illustrates an example of this functionality, wherein, in this example, a selection was made in the vicinity of the q12 label. As indicated by the phantom box 512 in FIG. 5B, the portion of displays 504*em* and 506*m* in the vicinity of where the selection was made have been expanded vertically.

Figure 6A:
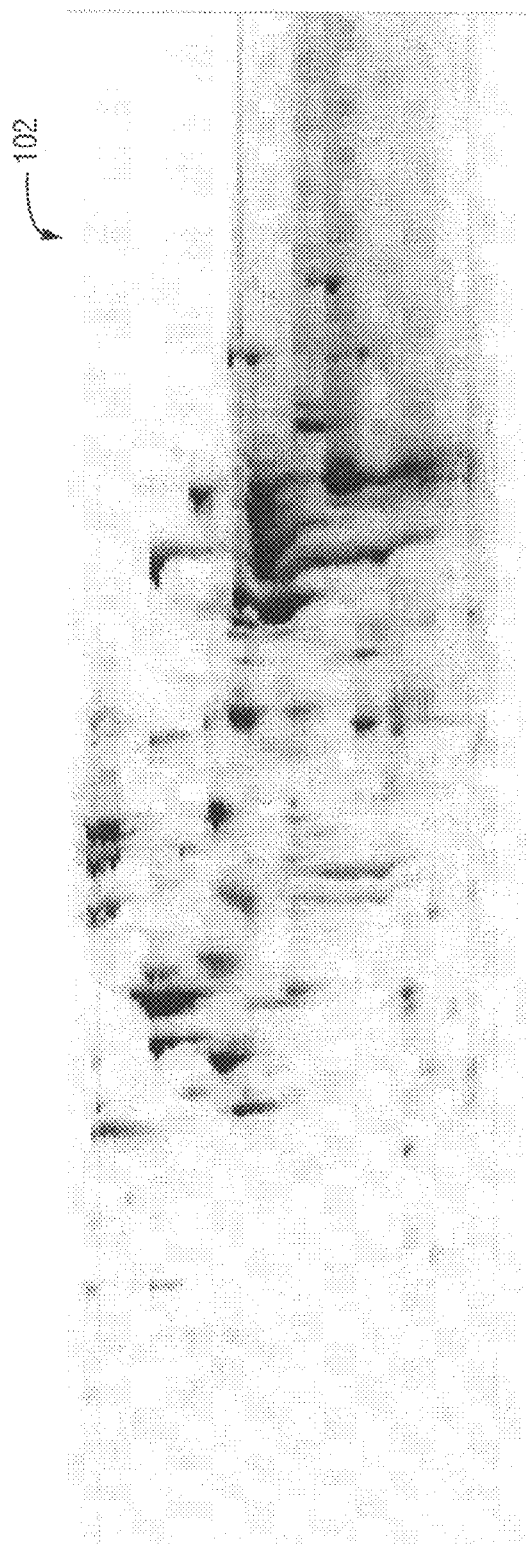
FIG. 6A shows an example of a visualization of plots generated from a two-dimensional high performance liquid chromatograph.
Figure 6B:
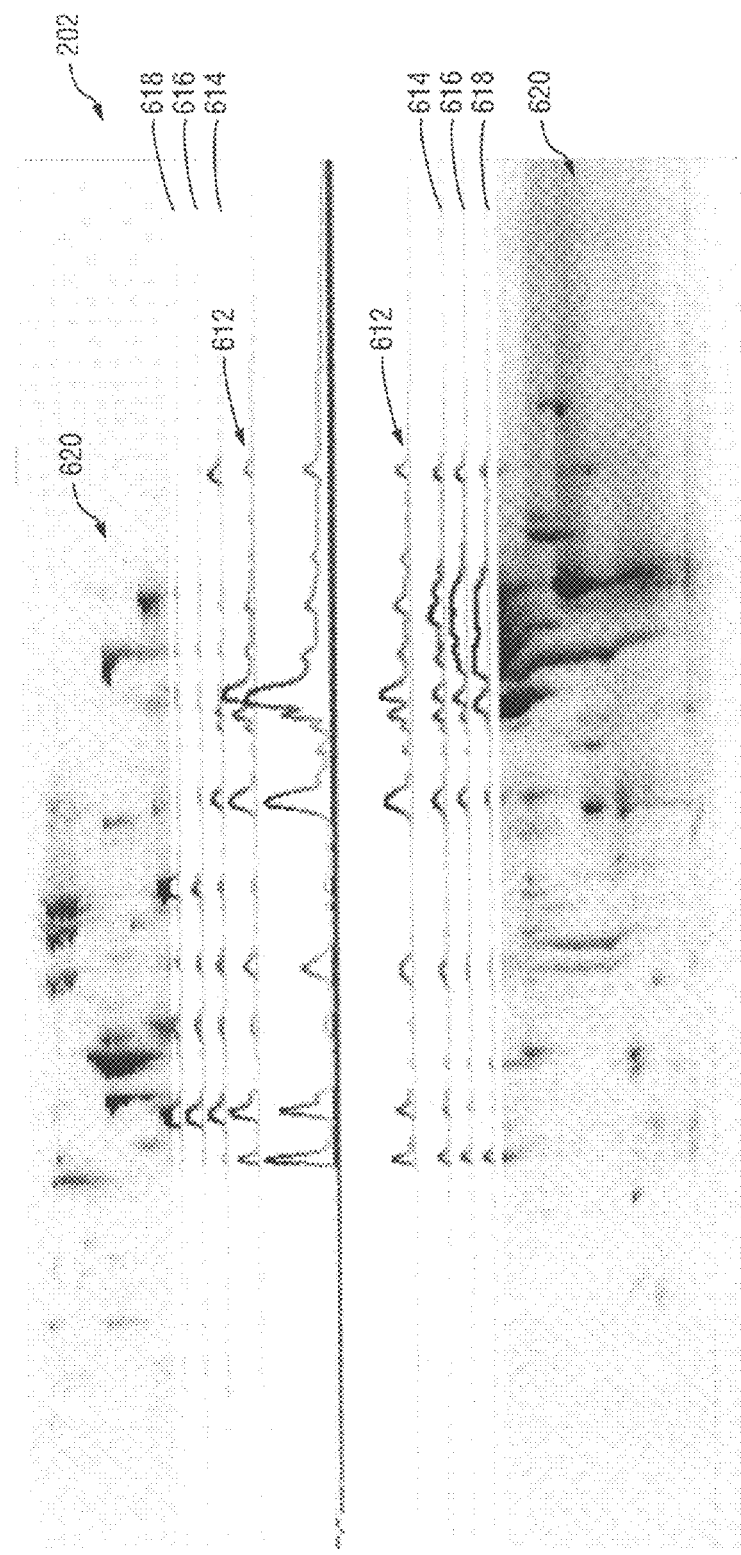
FIG. 6B is a visualization produced by selecting a region in the visualization of FIG. 6A for expansion.

Turning now to FIG. 6A, an example of a visualization 102 of plots generated from a two-dimensional high performance liquid chromatograph (2-D HPLC, Agilent 1100LC, Agilent Technologies, Inc., Palo Alto, Calif.) system with ultraviolet (UV) detector are shown in fully compressed form. FIG. 6B is a visualization 202 produced by selecting a region in the visualization 102 of FIG. 6A for expansion, similar to the description given above with regard to FIG. 2. Thus the location clicked on or otherwise selected in visualization 102 is expanded to the most zoomed or magnified representation 610 in visualization 202. That is, the line graph 610 selected by or nearest to the selection on the visualization 102 is the line graph that is displayed the largest in the expanded visualization 202 shown in FIG. 6B. Not only does the system magnify or zoom the selected line graph 610, but neighboring line graphs 612 are displayed in magnified view as well, although at a lesser vertical magnification or scale than what line graph 610 is displayed at. Similar to the example of FIG. 2, line graphs 612, 614, 616 and 618 are displayed in progressively decreasing smaller vertical scale, relative to the vertical scale of line graph 610 to communicate the visual impression of the transition from the zoomed line graph 610 down to the fully compressed line graphs 620. Although useful, it is noted that displaying the zoomed line graphs in progressively decreasing vertical scale in both directions away from the largest-zoomed line graph 610 is not necessary to the invention, as other display schemes may be alternatively employed. For example, line graphs 612, 614, 616 and 618 may all be displayed in the same vertical scale, although a smaller vertical scale than that which line graph 610 is displayed in. Or more or fewer line graphs may be displayed in a zoomed scale adjacent line graph 610. Or line graphs may be expanded adjacent only one side of the selected line graph 610 (either above or below). Of course there are many other display schemes that may be employed alternatively to those listed, as would be readily apparent to one of ordinary skill in the art. Further, note that the graphs of FIGS. 6A and 6B are not color coded, and thus the present invention is also useful for black and white or grayscale graphs.

Further, the user interface of the system may provide sorting features that are selectable by the user, for sorting the graphs (e.g., data from arrays) according to similarity of the line graphs or according to other sorting bases. For example, a sequence of graphs may be reordered by various clustering techniques or other metrics besides similarity sorting. Sorting based upon times during which the graphs were generated may be performed, and/or sorting on the basis of one or more other categories of classifying metadata may be performed such as different subtypes of cancer (e.g., benign, non-aggressive, aggressive), survival rates, different medical treatments, etc. As to similarity sorting, vector similarity sorting procedures described in application Ser. No. 10/403,762 (incorporated by reference above) may be used to order graphs, such that graphs displaying similar results are sorted together in the display 102, 202, 302, 502. Similarity sorting, clustering or other types of sorting may be carried out over the entire length of the graphs, or on a selected sub-set. For example, for aCGH data, a selected subset may be a particular chromosome or group of chromosomes. Further the user may select a custom subset of a graph upon which to similarity sort, such as a selected portion of a chromosome, or a group of selected portions of chromosomes.

Figure 7:
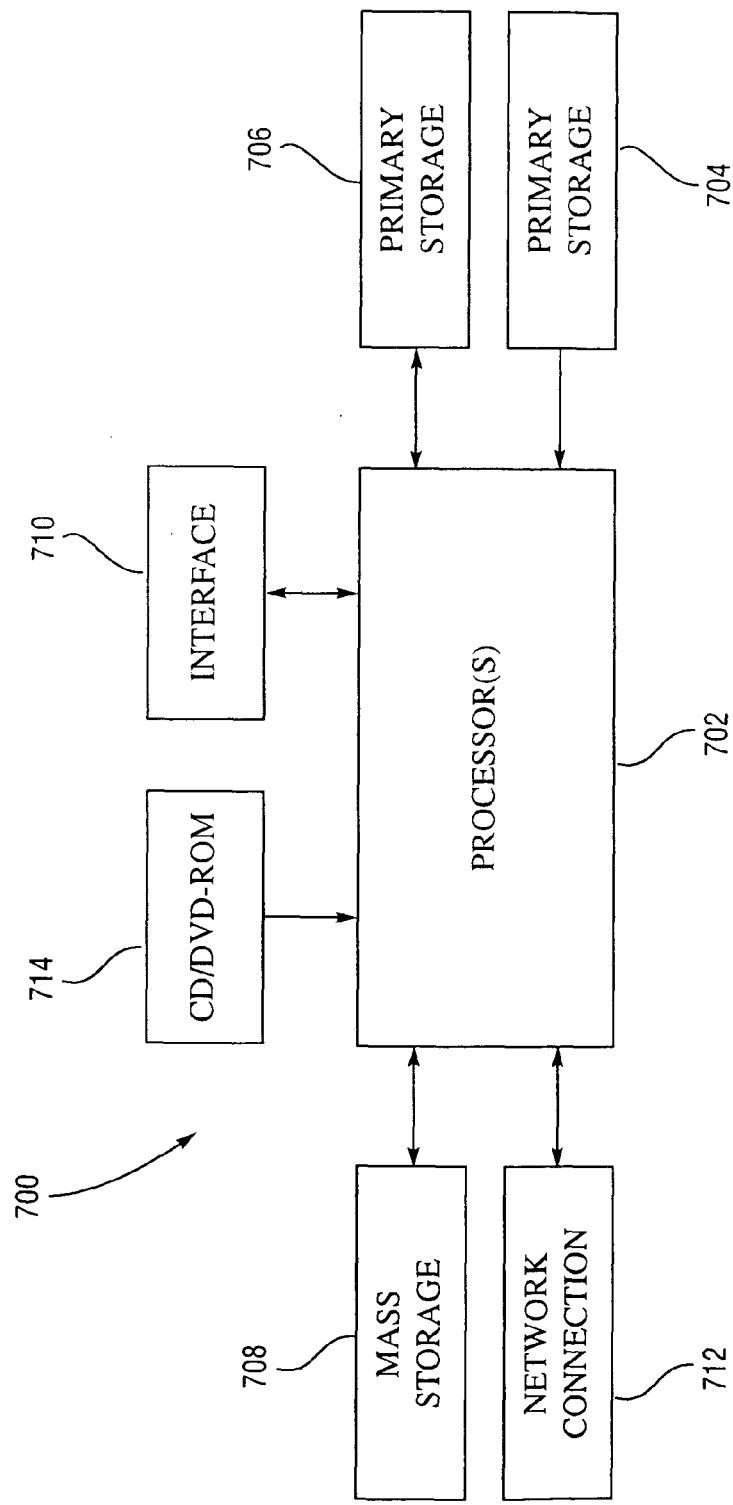
FIG. 7 illustrates a typical computer system in accordance with an embodiment of the present invention.

FIG. 7 illustrates a typical computer system in accordance with an embodiment of the present invention. The computer system 700 includes any number of processors 702 (also referred to as central processing units, or CPUs) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for calculating and plotting moving averages may be stored on mass storage device 708 or 714 and executed on CPU 708 in conjunction with primary memory 706.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A computer-implemented method of visualizing a collection of graphs, each graph comprising an ordered set of pairs of values, each pair of values having a first value indicative of a quantity along a first axis and a second value indicative of a corresponding quantity along a second axis, said method comprising:

provided a compressed display mode for each graph in which that graph is represented by a linear graph comprising a straight line along said first axis, said straight line having a visual property that varies along said first axis according to said second values;

providing an expanded display mode for each graph in which that graph is represented by a two-dimensional graph aligned along said first axis with said linear graph, said two-dimensional graph being characterized by a magnification along said second axis;

providing a compressed display in which all of said graphs are displayed in said compressed display mode, said straight lines corresponding to each graph being aligned with respect to one another and being presented in an ordered sequence;

receiving input from a user identifying one of said linear graphs; and providing an expanded display in which said identified linear display is replaced by said two-dimensional graph corresponding to that identified linear graph, said two-dimensional graph and said linear graphs remaining in said ordered sequence relative to one another.

2. The method of claim 1, wherein providing said expanded display further comprises replacing one of said linear graphs adjacent to said identified linear graph with said two-dimensional graph corresponding to that adjacent linear graph, said two-dimensional graph corresponding to said identified linear graph being displayed at a magnification greater than said magnification of said two-dimensional graph corresponding to said adjacent linear graph.

3. The method of claim 2, wherein a plurality of linear graphs adjacent at least one side of the identified linear graph are replaced by said corresponding two-dimensional graphs, said linear graphs and said two-dimensional graphs remaining in said ordered sequence, and wherein said magnifications of each of said two-dimensional graphs decrease as a function of distance from said identified linear graph in said ordered sequence.

4. The method of claim 1, further comprising zooming a portion of said expanded display to provide a visualization of that portion having a greater scale along said first axis than a remainder of said expanded display along said first axis.

5. The method of claim 4, wherein said zooming a portion comprises zooming a same portion, relative to said first axis, of each of said linear graphs.

6. The method of claim 1, wherein said graphs comprise line graphs.

7. The method of claim 1, wherein said graphs are plots based on microarray data.

8. The method of claim 1, wherein graphs comprise plots based on aCGH data.

9. The method of claim 1, further comprising generating said graphs by computing at least one of: moving averages, Z-scores, and p-values.

10. The method of claim 1, wherein said graphs comprise scatter plots.

11. The method of claim 1 further comprising receiving a scroll input for scrolling through said linear graphs, wherein the identified linear graph is varied by scrolling from one of said linear graphs to the next adjacent linear graph, in either of two directions, said scroll input comprising a user controlled pointer that moves over said linear graphs, each linear graph being replaced by said corresponding two-dimensional graph while said pointer is over that linear graph.

12. The method of claim 1 wherein said graphs are graphs of biological data that correlate to chromosomal locations.

13. The method of claim 1, further comprising sorting said graphs in response to user input and displaying a new order for said linear graphs in said ordered sequence.

14. The method of claim 12, wherein said compressed display includes graphic visualization of chromosomes of an organism, and wherein said graphs are divided according to correlations to said visualized chromosomes, said compressed display comprising a sub-collection of compressed displays adjacent each chromosome, each sub-collection containing graphs correlating to said chromosome adjacent to said sub-collection.

15. The method of claim 14, wherein data in each graph are displayed to correspond geographically to locations of the chromosome displayed adjacent thereto.

16. The method of claim 14, further comprising displaying a magnified visualization of a selected chromosome visualization and adjacent visualization of a sub-collection of graphs corresponding to the selected chromosome.

17. The method of claim 16, wherein said magnified visualization is displayed adjacent said visualization of chromosomes and adjacent sub-collections that have not been magnified.

18. The method of claim 16, wherein identifying one of said linear graphs is operable on said sub-collection in the magnified visualization.

19. The method of claim 16, further comprising scrolling through said magnified visualization, wherein a selected graph is varied by scrolling from one of said graphs to an adjacent graph, in either of two directions, and zooming each graph as that graph is scrolled over, while again returning said graph to said compressed display when said graph is no longer being scrolled over.

20. The method of claim 1, wherein said visual property comprises varying shades/intensities of colors in a manner that depends on said second values.

21. The method of claim 1, wherein at least one hundred of said line graphs are displayed.

22. The method of claim 1 wherein said second values of each of said graphs correspond to measurements of the same physical quantities, each graph corresponding to results from a different experiment that measures the same quantities on different samples.

23. A computer readable medium carrying one or more sequences of instruction for visualizing a collection of graphs, each graph comprising an ordered set of pairs of values, each pair of values having a first value indicative of a quantity along a first axis and a second value indicative of a corresponding quantity along a second axis, wherein execution of said one or more sequences of instructions by one or more processors causes the one or more processors to perform a process comprising:

providing a compressed display mode for each graph in which that graph is represented by a linear graph comprising a straight line along said first axis, said straight line having a visual property that varies along said first axis according to said second values, providing an expanded display mode for each graph in which that graph is represented by a two dimensional graph aligned along said first axis with said linear graph, said two-dimensional graph being characterized by a magnification along said second axis;

providing a compressed display in which all of said graphs are displayed in said compressed display mode, said straight lines corresponding to each graph being aligned with respect to one another and being presented in an ordered sequence;

receiving input from a user identifying one of said linear graphs; and providing an expanded display in which said identified linear graph is replaced by said two-dimensional graph corresponding to that identified linear graph, said two-dimensional graph and said linear graphs remaining in said ordered sequence relative to one another.

24. The computer readable medium of claim 23 wherein said visual property comprises a variation in color of said line, said color variation being determined by said second values.

25. The computer readable medium of claim 23 wherein said visual property comprises a variation in density of said line, said density variation being determined by said second values.

26. The computer readable medium of claim 23 wherein said two-dimensional graph replacing said identified linear graph has a scale along said first axis that is the same as that of said replaced linear graph.

27. The computer readable medium of claim 23 wherein providing said expanded display further comprises replacing one of said linear graphs adjacent to said identified one of said linear graphs in said ordered sequence by said two-dimensional graph corresponding to that linear graph, said two-dimensional graph corresponding to said adjacent linear graph having a scale along said second axis that is less than that of said two-dimensional graph by said user input.

28. The computer readable medium of claim 23 wherein providing said expanded display further comprises replacing a plurality of said linear graphs adjacent to said identified one of said linear graphs in said ordered sequence by said two-dimensional graphs corresponding to those linear graphs, said two-dimensional graphs corresponding to each of said adjacent linear graphs having a scale along said second axis that varies monotonically according to a relative position of that two-dimensional graph with respect to said linear graph identified by said user input.

29. The computer readable medium of claim 23 wherein said method further comprises receiving input from a user specifying a region along said first axis and altering a scale of said compressed and expanded displays along said first axis in said specified region.

30. The computer readable medium of claim 23 wherein all of said second values correspond to the same physical quantity.

31. The computer readable medium of claim 30 wherein said physical quantity comprises a quantity derived from microarray data or aCGH data.

32. The computer readable medium of claim 23 wherein said second values of one of said graphs is computed by said computer using moving averages, Z-scores, or p-values.

33. The computer readable medium of claim 23 wherein said two-dimensional graph corresponding to said identified linear graph comprises a line graph in which said line comprises said visual property that varies along said first axis according to said second values.

34. The computer readable medium of claim 23 wherein said expanded display comprises additional information about said graph corresponding to said two-dimensional graph corresponding to said identified linear graph.

* * * * *